United States Patent [19]

Stempel

[11] 4,370,133
[45] Jan. 25, 1983

[54] DENTURE MEANS AND METHOD

[75] Inventor: John A. Stempel, Chester, N.J.

[73] Assignee: Cavitron Corporation, Palo Alto, Calif.

[21] Appl. No.: 469,934

[22] Filed: May 14, 1974

[51] Int. Cl.³ .............................................. A61C 13/22
[52] U.S. Cl. .................................................... 433/171
[58] Field of Search ......................................... 433/171

[56] References Cited

U.S. PATENT DOCUMENTS

| 3,813,777 | 6/1974 | Handel | 32/2 |
| 3,838,513 | 10/1974 | Katz | 32/2 |
| 3,846,911 | 11/1974 | Wichner | 32/2 |

FOREIGN PATENT DOCUMENTS 1382796 5/1975 United Kingdom ..................... 32/4

Primary Examiner—Robert Peshock
Attorney, Agent, or Firm—Thomas R. Boland

[57] ABSTRACT

Disclosed herein is an improved tray for use in producing a denture either in-situ or by use of a model of the patient's mouth. The tray comprises a basic tray of disposable material approximating the shape of either the palate or the lower gums and having inner and outer wall portions integral therewith and forming a trough defining a gum receiving portion with a U-shape opening in the trough mounting, means for mounting a plurality of artificial teeth approximating the teeth found in either the upper or lower portion of the mouth, the mounting means having a flange portion made of dental acrylic which rests on the sides of the trough adjacent the U-shaped opening with the plurality of the teeth extending through the opening. The process of producing the denture comprises placing the tray in to a patient's mouth, pressing the deformable walls of tray against the surfaces of the patient's mouth to approximate the shape of the upper or lower part of the mouth, withdrawing the shaped tray; placing a moldable acrylic base denture forming resin in the tray; pressing the tray holding the resin against the portion of the patient's mouth until the resin cures in-situ to conform to the shape of the adjacent surfaces of the patient's mouth, withdrawing the tray containing the cured resin from the patient's mouth, and separating the tray from this cured resin, whereby the denture remains comprising the cured resin and the attached flange and artificial teeth.

8 Claims, 7 Drawing Figures

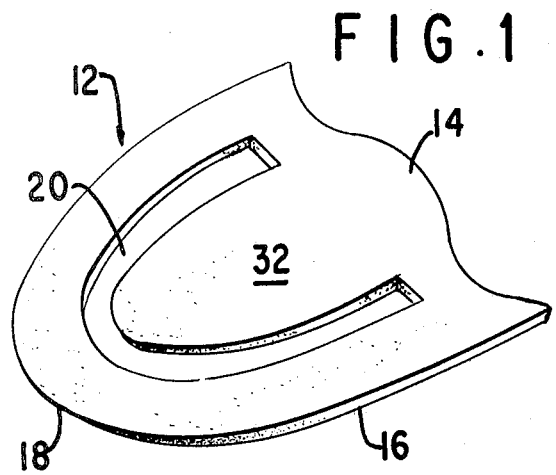
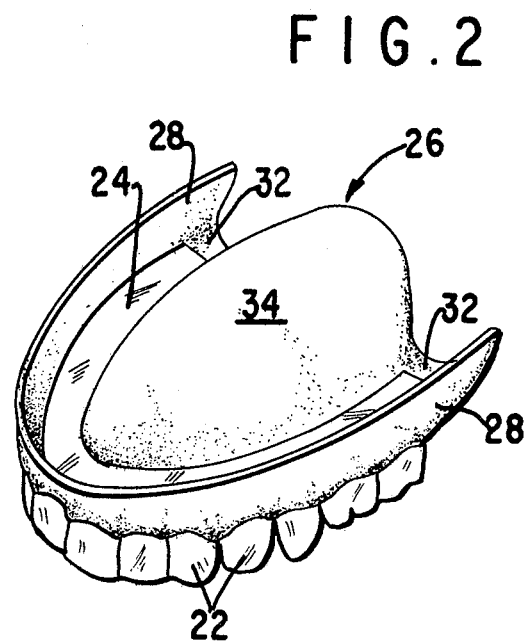
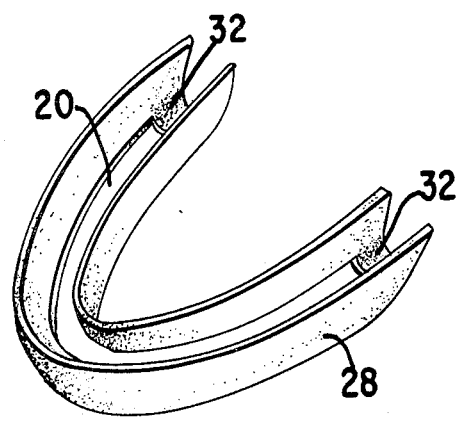
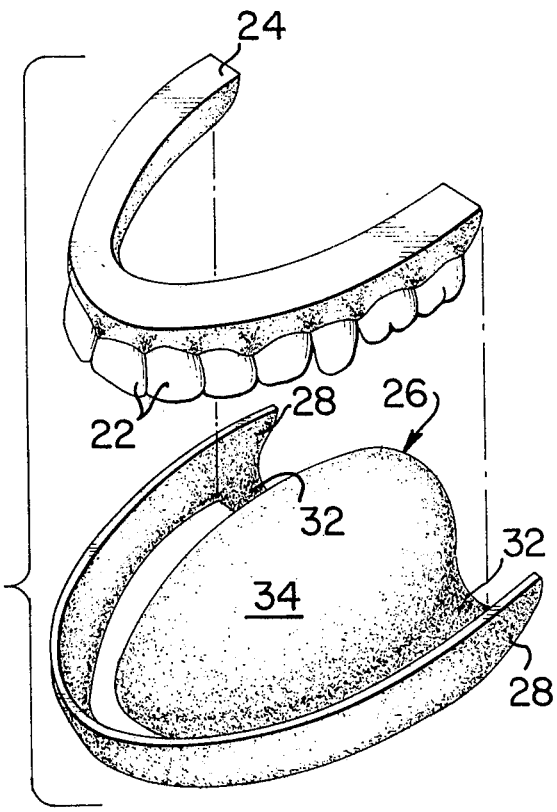

DENTURE MEANS AND METHOD

BACKGROUND OF THE INVENTION

This application relates to a means and an associated method for producing an artificial denture. More particularly this application relates to a novel tray for use in preparing a denture by a method also described herein.

In U.S. Pat. No. 3,460,252 there is described various means and methods for forming a denture in-situ in the mouth of a dental patient. In U.S. Pat. No. 3,621,575 there is described various improvements in or relating to in-situ dentures involving the use of a gutter shim or shims having a gutter portion and/or different curable denture-forming materials. In copending application, Ser. No. 126,507 now abandoned, filed Mar. 22, 1971, there are described means and methods for making an in-situ denture involving the use of a former or adapted tray comprising a tray and impression material in which there has been formed a general impression of the patient's gums by taking a general impression of the gums through a spacer in a tray holding false teeth and having impression material therein.

Such prior art describes various ways of producing an effective denture by in-situ fitting or molding of the denture in the patient's mouth. My invention is of a novel tray and method for producing such an improved denture.

SUMMARY OF THE INVENTION

We have developed an improvement in our means and method for producing a denture either in-situ in the mouth of a dental patient or against a model of the gums. The means for producing the denture comprises a tray or former having an opening therein for receiving a mounting means for supporting a plurality of artificial teeth, the teeth projecting through the opening. More particularly our tray for forming a denture comprises a basic tray comprising an inner wall portion and an outer wall portion integral therewith and forming a trough defining a gum receiving portion. The basic tray has an opening there through between the inner and outer wall portions. Mounting means for mounting a plurality of artificial teeth is positioned in the trough portion, the mounting means having a flange portion overlapping the opening in the tray between the inner and outer wall portions whereby the artificial teeth project through the opening.

The method of producing a denture according to our invention using the tray having a flange mounting a plurality of artificial teeth comprises pressing the deformable portions of the tray against the appropriate part of the patient's mouth either to approximate the upper or lower part of the mouth; then withdrawing the shaped tray from the mouth; placing a moldable acrylic base denture forming resin in the tray; and pressing the tray holding the resin against the patient's mouth until the resin cures in-situ. The tray and cured resin is removed from the mouth and the tray separated from the cured resin. The flange and artificial teeth are permanently bonded to the cured resin to form the denture. A shim may be placed in the moldable resin before the tray is pressed against the mouth and is a preferred method of molding the denture according to our invention.

An object of the present invention is to provide improvement in the formation of dentures, including particularly the in-situ formation of dentures.

Another object is to provide new and improved devices for use in the formation of dentures.

Another object is to provide new and improved methods for the formation of dentures.

A further object is to provide novel and efficient means for making a tray for use in the formation of dentures.

A still further object is to provide improved and more efficient procedures for in-situ denture formation of dentures.

These and other objects of the present invention will be evident from the following description of the invention and accompanying drawings.

BRIEF DESCRIPTION OF THE DRAWINGS

FIG. 1 is a perspective view of a formable upper tray without teeth.

FIG. 2 is a perspective view of the formable upper tray with teeth mounted therein.

FIG. 3 is a perspective view of a lower tray without teeth.

FIG. 4 is an exploded perspective view of the preformed unitary structure of the present invention being inserted into the formable upper tray

DESCRIPTION OF THE PREFERRED EMBODIMENT

Figure 5A:
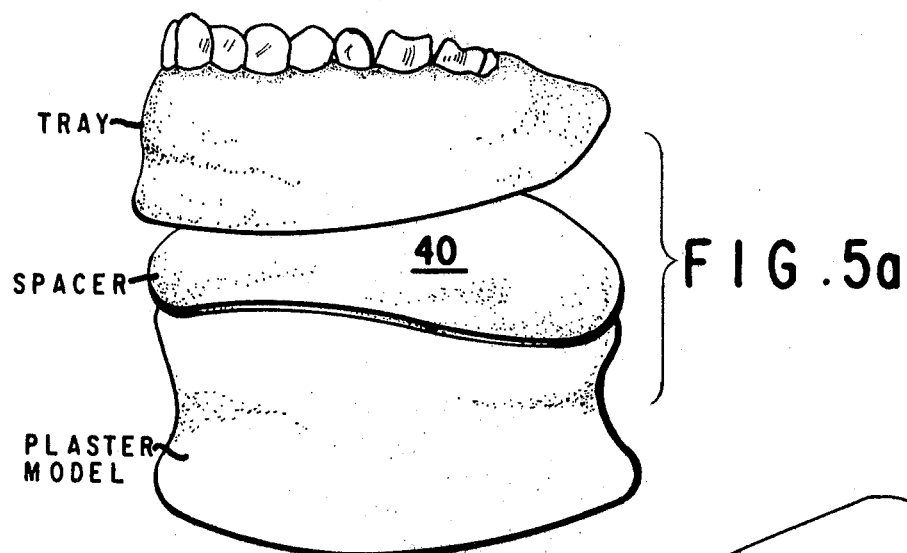
FIGS. 5a to 5c shows the method according to the invention.
Figure 5B:
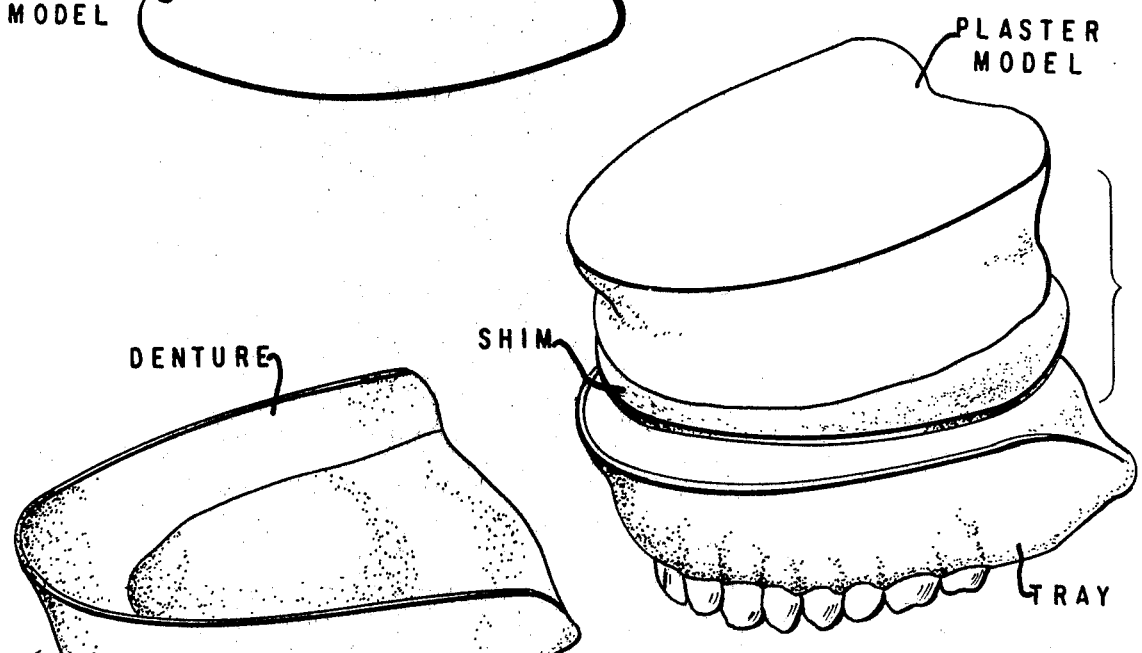
Figure 5C:
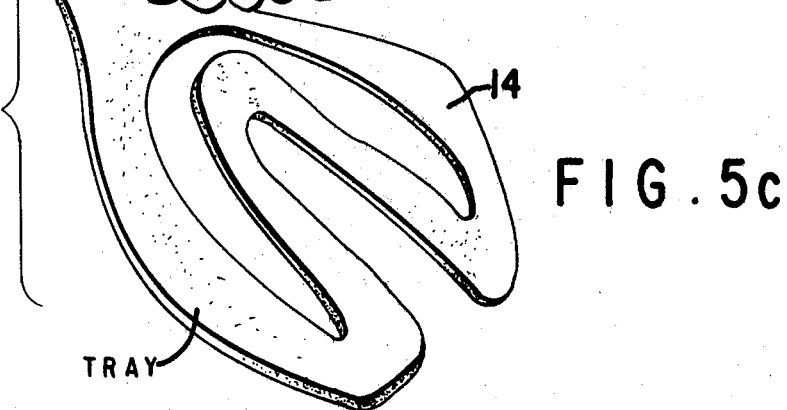

In accordance with the present invention, a tray is formed by utilizing a sheet of formable material which is shaped using a suitable mold, dental stone or die to approximate either the lower or upper part of a patient's mouth. Preferable an U-shaped opening is cut in the tray for inserting artificial teeth mounting means therethrough. Specifically the artificial teeth approximate a set as found in the lower or upper part of a paient's mouth and are individually mounted on a mounting flange. The flange is preferably made of a pigmented dental acrylic resin which is bondable to the dental acrylic such as that artificial teeth are conventionally formed.

The tray is preferably formed from any sheet material which may be readily shaped and which will retain its shape after such deformation. Such a sheet may be shaped at either room temperatures or at somewhat elevated temperatures. Thus the terminology using words as "formable" and shapeable and the like as used herein indicate the property of such a material.

Referring now to the drawings, FIG. 1 illustrates a flat sheet 12 of tray forming material generally semicircular in shape and having a flat side 14 curved sides 16 and a front portion 18, the latter two merging which can be shaped to a new form at either room or a somewhat elevated temperature and will hold the new set. One such preferred material is dental baseplate wax which is commercially available in sheet form. Such a wax may be made from a mixture of parafin wax and beeswax. This material in sheet form is formable at room temperature and thus will not readily crumble under such handling. While the wax sheet may be of any convenient thickness it has been found that a preferred thickness is in the range from about 0.060 to 0.085 inches. In preparing the flat wax sheet 12, a U-shape opening is die-cut confirming in general shape to the arrangement of a set of teeth in a mouth. A set of individual artificial teeth 22 mounted in a flange 24 and conforming in shape, number and appearance to the set of 14 teeth found in either the upper or lower jaw of the patient is next inserted through the opening 20 with the teeth protruding therethrough one one side and the side of the flange 24 resting on the other side of the sheet adjacent the opening. The flat wax sheet and mounted teeth are put into a dental flask, that is, a press of the sort used in dentistry and the flat sheet is shaped to conform to the general form of either the upper or lower part of the mouth. Prior to puting the wax sheet into the dental "flask" the sheet is preferably softened at a somewhat elevated temperature of about 120° C. Upon removal from the flask the tray is in its functional form as shown in FIGS. 2 and 3 of the drawing.

FIG. 2 shows a tray 26 suitable for use in preparing a denture for the upper part of the mouth. The tray has an outer wall 28 upstanding along the sides 16 and front 18 of the sheet to fit the outside of the patient's upper gums. The inside surface of the sheet is shaped by the dental flask to approximate the inner side of the gum by an inner wall 30 upraised thereby forming a trough 32 in which the flange mounted teeth are seated. That portion joining the inner upstanding wall 32 of the tray approximates the palate of the patient and is herein denominated as the palate portion 34 of the tray. The flange 24 mounting the individual artificial teeth 22 is a unitary structure which ultimately becomes part of the finished denture according to the process of this invention.

The flange mounting the teeth is produced as follows. Individual teeth 22 procured or produced according to conventional and well known methods are inserted into a plastic jig or then suitable molding equipment. The individual artificial teeth are made of any suitable material. Presently porcelain or plastic teeth are commonly available. Preferably the teeth used herein are those made of plastic and are specifically those made of dental teeth acrylic. The teeth are arranged in the normal sequence of 14 artificial human teeeth, i.e. 4 incisors, 2 canines, 4 premolars and 4 molars. The jig is a plastic form made of a suitable relatively rigid plastic sheet as for instance ethylene vinyl acetate (EVA) and molded to hold the teeth in their proper relative position. For economy the molded plate form is supported on the base of dental plaster or silicone rubber. The jig supports the set of teeth with their bottoms facing upward and extending a limited distance into a shaped trough. The next step after emplacing the teeth is to pour commercially available pink dental acrylic resin into the trough and over the teeth to a height of about 1/16–150 inch. Following this step a counter-die is placed over the trough to apply pressure to the poured resin while the teeth are secured in place. By applying pressure the resin is caused to flow into the available spaces, at the same time minimizing air entrapment and bubbles. After a suitable amount of time to allow the dental acrylic resin to fully cure the counter-die is lifted off and the molded flange 24 mounting the artificial teeth removed from the jig. The flange mounted teeth are then used in combination with the flat wax sheet as described above to produce the tray according to the present invention. The tray as described and shown in FIGS. 2 or 3 is now suitable for use in preparing the denture according to the method of the present invention.

To prepare the denture, a dental impression of the patient's mouth either upper palate and gums or lower gums is taken in the conventional manner using alginate or other suitable impression material. A reverse model in dental stone is then prepared using the impression so made. The tray according to the present invention is then first softened in warm water, i.e. at a temperature of about 120° F. At the same time a spacer in the form of a flat wax sheet of the same material as the tray and also softened in warm water is first placed and fitted over the dental stone model of the impression. The softened tray is then placed over the fitted spacer and hand pressure applied over the tray. After this first fitting of the tray to the dental stone model of the patient's gums and/or palate the tray is removed and the spacer discarded. The purpose of this fitting step was to conform the tray generally to the patient's mouth while leaving sufficient room by utilization of the spacer to provide space within the tray in which to mold the denture in-situ.

Following removal of the fitted tray from over the dental stone mold, material for molding the denture is prepared. Specifically a "hard" dental acrylic (tinted pink) resin is prepared from commercially available dental resins by mixing the liquid and powder components of the resin. First the woven acrylic shim is soaked or wetted in acrylic monomer. Then a small portion of the mixed hard resin liquid and powders applied over the teeth on the tray. The wetted shim is then placed over the plaster mold. Then the remainder of the mixed hard resin (liquid and powder) is applied evenly over the top of the shim as it is draped on the plaster mold. The shim and mold are then applied with light pressure to the tray containing the minimal application of the hard mixed resin. The plaster mold is removed immediately after the shim is fitted into the tray. A "semi-rigid" dental acrylic resin also tinted pink is prepared for use by mixing the acrylic resin powder and liquid together monomer. (First the cloth shim is cut to fit within the internal dimensions of the tray and over the flange mounted teeth. Then the "hard" acrylic resin is poured into the tray. Immediately the shim is placed over the hard uncured acrylic resin layer). The "semi-rigid" dental acrylic resin poured over the shim into the tray. The tray is then placed into the patient's mouth and fitted into position against the appropriate surfaces thereof with the "semi-rigid" resin layer contacting to gum and mouth surfaces. The tray is so held in-situ in the patient's mouth for a period of about six (6) minutes to allow the resin to cure and set in its fitted position. The tray is then removed from the mouth and allowed to stand for a sufficient time to polymerize (cure) the resin fully. This time may be at least another 2 minutes, but there is of course no time limit. The tray may then be removed to obtain the semi-finished denture.

To remove the tray or rather that part of the tray which is not incorporated into the denture, the tray and semi-finished denture is soaked in warm water (at about a temperature of 140° F.) After being so heated the wax portion of the tray is easily stripped from the semi-finished denture. After stripping the wax, what remains is essentially a fully formed and sem-finished denture. Final finishing of the denture is accomplished by polishing the surfaces of the molded denture in the conventional manner.

Having thus fully described the preferred embodiment of my invention and wishing to cover these variations and modifications which would be apparent to those skilled in the art but without departing from either the spirit or scope thereof.

I claim:

1. An assembly for forming a denture in the mouth of a dental patient comprising a tray having inner and outer walls made of formable material and approximating the shape of the patient's gums, a trough between said walls defining therewith a gum-receiving portion, a substantially U-shaped continuous slot formed in the bottom of said trough, said assembly further including a preformed unitary structure including pre-arranged individual artificial teeth and means for removably mounting said teeth in the slot of said tray, said mounting means including a preformed flange molded about the bases of said teeth to fixedly support said teeth in said preformed unitary structure, said flange extending beyond said slot onto said walls to support said teeth in said tray so that said teeth project through said slot.

2. The assembly in accordance with claim 1 wherein said inner walls are connected by said formable material to form a palate whereby the tray is suitable for use in forming a denture for the upper portion of the mouth.

3. The assembly in accordance with claim 1 wherein said formable material is dental baseplate wax.

4. The assembly in accordance with claim 1 wherein said preformed flange is formed of dental acrylic resin molded about the bases of said artificial teeth.

5. A method of forming an artificial denture for the mouth of a dental patient employing a tray having a gum-receiving portion with a U-shaped continuous slot formed therein, and a preformed unitary structure including a flange mounting a plurality of pre-arranged artificial teeth on said tray with said teeth projecting through said slot, the method comprising:

placing said preformed unitary structure in the gum-receiving portion of said tray so that said teeth project through said slot, placing a deformable sheet as a spacer over said tray, applying pressure to said tray having said spacer therein to conform said tray to the gums of a patient with the spacer between the surfaces of said tray and of said gums, removing said tray from said gums, applying a suitable amount of dental acrylic resin to said tray, placing said tray in contact with said gums with said dental acrylic resin adjacent said gum surfaces, simultaneously forcing said tray against said gums while allowing said dental acrylic resin to harden, removing said tray from said gums, and separating said tray from said hardened acrylic resin whereby said preformed unitary structure and said hardened acrylic resin form a unitary denture.

6. The method of claim 5 further including the step of fitting a shim into said tray in contact with said dental acrylic resin prior to placing said tray in contact with said gums or model.

7. The method of claim 6 wherein said shim is formed of woven acrylic fibers, and wherein said step of fitting said shim into said tray additionally comprises the step of soaking said shim in a solution of acrylic monomer.

8. The method of claim 7 wherein said step of applying a suitable amount of dental acrylic resin into said tray includes the steps of disposing in said tray a first layer of dental acrylic resin, then disposing in contact therewith a shim having a first surface and an opposite surface with said first surface in wetting contact with said first layer, and then disposing a second layer of dental acrylic resin in contact with said opposite shim surface.

* * * * *